United States Patent [19]

Sasse et al.

[11] Patent Number: 4,765,824
[45] Date of Patent: * Aug. 23, 1988

[54] PYRIMIDYL-THIO-CARBOXANILIDES

[75] Inventors: Klaus Sasse, Bergisch Gladbach; Reiner Fischer, Monheim; Hermann Hagemann; Hans-Joachim Santel, both of Leverkusen; Robert R. Schmidt, Bergisch Gladbach; Robert H. Strang, Düsseldorf, all of Fed. Rep. of Germany

[73] Assignee: Bayer Aktiengesellschaft, Leverkusen, Fed. Rep. of Germany

[*] Notice: The portion of the term of this patent subsequent to Dec. 9, 2003 has been disclaimed.

[21] Appl. No.: 934,064

[22] Filed: Nov. 21, 1986

[30] Foreign Application Priority Data

Dec. 13, 1985 [DE] Fed. Rep. of Germany ....... 3344209

[51] Int. Cl.4 .................. A01N 43/48; C07D 239/02
[52] U.S. Cl. ......................................... 71/92; 544/316; 544/311; 544/312
[58] Field of Search ................ 544/316, 311, 312; 71/92

[56] References Cited

U.S. PATENT DOCUMENTS 4,627,871 5/1985 Sasse et al. .................... 544/318

FOREIGN PATENT DOCUMENTS 0168608 1/1986 European Pat. Off. ............ 544/316
109170 10/1974 Fed. Rep. of Germany ...... 544/316

OTHER PUBLICATIONS

Morrison and Boyd, *Organic Chemistry*, 1973, pp. 742, 746.

Primary Examiner—Mary C. Lee
Assistant Examiner—Zinna Northington
Attorney, Agent, or Firm—Sprung Horn Kramer & Woods

[57] ABSTRACT

A pyrimidyl-thio-carboxanilide of the formula (I),

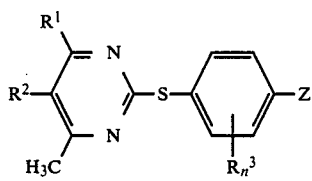

in which
$R^1$ represents hydrogen or halogen, alkyl, alkoxy or alkylthio having 1 to 6 carbon atoms in each case, trifluoromethyl, or phenyl which is unsubstituted or mono- or poly-substituted, identically or differently, by halogen, methyl, ethyl, methoxy or trifluoromethyl,
$R^2$ represents hydrogen, halogen, alkyl having 1 to 6 carbon atoms or trifluoromethyl,
$R^3$ represents halogen, methyl or methoxy,
n represents an integer 0, 1 or 2, and
Z represents the radical

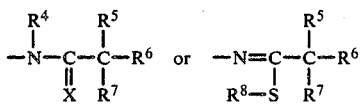

where
X represents oxygen or sulphur,
$R^4$ represents hydrogen or hydroxyl, alkyl or alkoxy having 1 to 6 carbon atoms in each case, alkenyl or alkynyl having 3 to 6 carbon atoms in each case, with the proviso that $R^4$ does not represent hydrogen when X represents oxygen,
$R^5$ represents hydrogen, halogen or alkyl having 1 to 6 carbon atoms which is unsubstituted or mono- or poly-substituted by halogen or
$R^4$ and $R^5$, together with the carbon atom and the nitrogen atom to which they are bonded, form a 3- to 8-membered heterocyclic ring which is unsubstituted or mono- or poly-substituted, identically or differently, by halogen, methyl or ethyl and which may contain one or more double bonds,
$R^6$ and $R^7$, independently of one another, represent halogen or alkyl having 1 to 6 carbon atoms which is unsubstituted or mono- or poly-substituted by halogen,
$R^6$ and $R^7$, together with the carbon atom to which they are bonded, form a 3- to 8-membered ring which may also contain oxygen and/or sulphur atoms as ring members in addition to carbon, and which is unsubstituted or mono- or poly-substituted by halogen, methyl or ethyl and which may contain one or more double bonds, and
$R^8$ represents hydrogen, alkyl having 1 to 6 carbon atoms, which is unsubstituted or mono- or poly-substituted by halogen, alkenyl or alkynyl having 3 to 6 carbon atoms in each case, processes for their preparation, herbicidal compositions and methods for combating weeds using such pyrimidyl-thio-carboxanilides.

8 Claims, No Drawings

PYRIMIDYL-THIO-CARBOXANILIDES

BACKGROUND OF THE INVENTION

1. Field of the Invention

The present invention relates to new pyrimidyl-thiocarboxanilides, several processes for their preparation and their use as herbicides.

2. Background Information

It is already known that certain carboxanilides have herbicidal properties (cf. R. Wegler "Chemie der Pflanzenschutz-und Schädlingsbekämpfungsmittel [The chemistry of plant-protection agents and pesticides]" Vol. 2, pages 311–314, Springer-Verlag, Berlin 1970). Thus, propion-3,4-dichloroanilide, for example, can be employed for combating weeds. The action of this compound is good, but some weeds are not always covered completely when small amounts are applied. In addition, the selectivity leaves something to be desired in some cases.

Furthermore, it is known that numerous 2-pyrimidinyl ethers and 2-pyrimidinyl thioethers are suitable as herbicides (cf. Japanese Preliminary Published Application No. 9,474/1967, U.S. Pat. No. 3,126,271 and U.S. Pat. No. 3,250,775). For example, 2-phenoxy-4,6-dimethyl-pyrimidine and 2-(4-chlorobenzylmercapto)-4,6-dimethyl-pyrimidine can be used to combat weeds. The herbicidal potency of these substances is, however, not always adequate.

Furthermore, it is known that lower acyl derivatives of 4-pyridyloxy-(or thio)-anilines have herbicidal properties (cf. DE-OS (German Published Specification) No. 2,501,648, Japanese Preliminary Published Application No. 55/122,763 and Japanese Preliminary Published Application No. 56/123,970). In addition, acyl derivatives of 4-pyrimidyloxy-anilines which are active as herbicides and which are substituted in the 5-position of the pyrimidyl radical by halogen or trifluoromethyl, but do not contain substituents in the 4 and 6 positions, are also known (cf. Japanese Preliminary Published Application No. 56/029,576). However, the effectiveness of these substances is not always satisfactory for practical purposes.

SUMMARY OF THE INVENTION

New pyrimidyl-thio-carboxanilides formula (I)

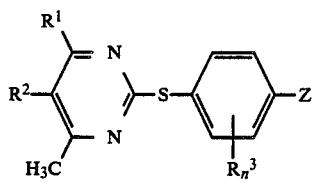

in which
$R^1$ represents hydrogen or halogen, $C_1$ to $C_6$ alkyl, $C_1$ to $C_6$ alkoxy or $C_1$ to $C_6$ alkylthio, trifluoromethyl, or phenyl which is unsubstituted or mono- or polysubstituted, identically or differently, by halogen, methyl, ethyl, methoxy or trifluoromethyl,
$R^2$ represents hydrogen, halogen, alkyl having 1 to 6 carbon atoms or trifluoromethyl,
$R^3$ represents halogen, methyl or methoxy,
n represents an integer 0, 1 or 2, and
Z represents the radical

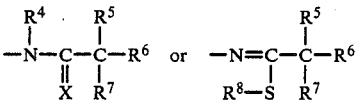

where
X represents oxygen and sulphur,
$R^4$ represents hydrogen or hydroxyl, $C_1$ to $C_6$ alkyl or $C_1$ to $C_6$ alkoxy, $C_3$ to $C_6$ alkenyl or $C_3$ to $C_6$ alkynyl, with the proviso that $R^4$ does not represent hydrogen when X represents oxygen,
$R^5$ represents hydrogen, halogen or alkyl having 1 to 6 carbon atoms which is unsubstituted or mono- or polysubstituted by halogen or
$R^4$ and $R^5$, together with the carbon atom and the nitrogen atom to which they are bonded, form a 3- to 8-membered heterocyclic ring which can be identically or differently mono- or polysubstituted by halogen, methyl or ethyl and which may contain one or more double bonds.
$R^6$ and $R^7$ independently of one another, represent halogen or alkyl having 1 to 6 carbon atoms which is unsubstituted or mono- or polysubstituted by halogen or
$R^6$ and $R^7$, together with the carbon atom to which they are bonded, form a 3-to 8-membered ring which may also contain oxygen and/or sulphur atoms as ring members in addition to carbon, and which can be identically or differently mono- or polysubstituted by halogen, methyl or ethyl and which may contain one or more double bonds, and
$R^8$ represents hydrogen, alkyl having 1 to 6 carbon atoms, in which is unsubstituted or mono- or polysubstituted by halogen, $C_3$ to $C_6$ alkenyl or $C_3$ to $C_6$ alkynyl,
have now been found.

Furthermore, it has been found that pyrimidyl-thio-carboxanilides of the formula (I) are obtained with the aid of the process described below:

(a) pyrimidyl-thio-carboxanilides of the formula (Ia),

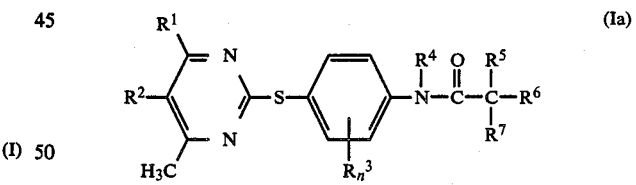

in which $R^1$, $R^2$, $R^3$, $R^4$, $R^5$, $R^6$, $R^7$ and n have the abovementioned meaning are obtained (a-α) when 4-(pyrimidyl-thio)-anilines of the formula (II)

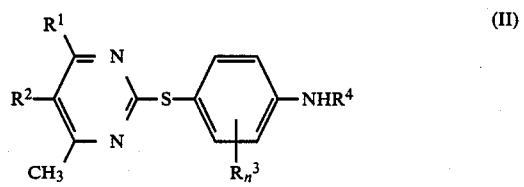

in which $R^1$, $R^2$, $R^3$, $R^4$ and n have the abovementioned meaning, are reacted with carboxylic acid derivatives of the formula (III),

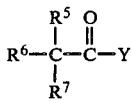 (III)

in which

R⁵, R⁶ and R⁷ have the abovementioned meaning and

Y represents hydroxyl, halogen, acyloxy, benzenesulphonyl or toluenesulphonyl, if appropriate in the presence of a diluent and if appropriate in the presence of an acid binder, or (a-β) the pyrimidyl-thio-carboxanilides of the formula (Ia-1),

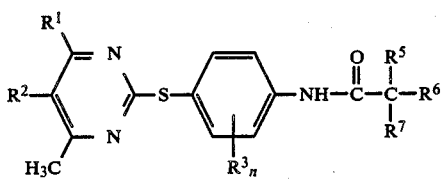 (Ia-1)

in which $R^1$, $R^2$, $R^3$, $R^5$, $R^6$, $R^7$ and n have the abovementioned meaning, which can be obtained according to process (a-α) are reacted with alkylating agents of the formula (IV)

$$R^4—U \quad (IV)$$

in which

R⁴ has the abovementioned meaning and

U represents an electron-withdrawing leaving group, if appropriate in the presence of a diluent and if appropriate in the presence of an acid binder, or (b) pyrimidyl-thio-carboxanilides of the formula (Ib),

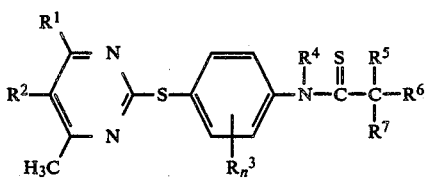 (Ib)

in which $R^1$, $R^2$, $R^3$, $R^4$, $R^5$, $R^6$, $R^7$ and n have the abovementioned meaning, are obtained when the pyrimidyl-thio-carboxanilides of the formula (Ia),

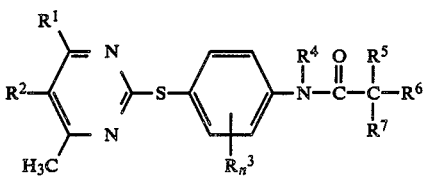 (Ia)

in which $R^1$, $R^2$, $R^3$, $R^4$, $R^5$, $R^6$, $R^7$ and n have the abovementioned meaning, which can be obtained according to the processes (a/versions α and β) are reacted with sulphurization agents in the presence of a diluent, or (c) pyrimidyl-thio-carboxanilides of the formula (Ic),

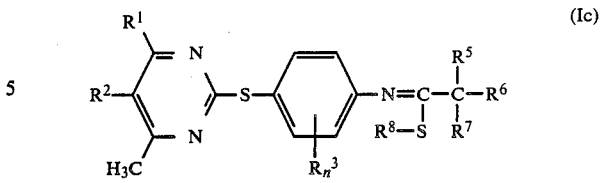 (Ic)

in which $R^1$, $R^2$, $R^3$, $R^5$, $R^6$, $R^7$, $R^8$ and n have the abovementioned meaning, are obtained when the pyrimidyl-thio-carboxanilides of the formula (Ib) which can be obtained according to process (b) are reacted with alkylating agents of the formula (V);

$$R^8—U \quad (V)$$

in which R⁸ and U have the abovementioned meaning, if appropriate in the presence of a diluent and if appropriate in the presence of an acid binder.

Finally, it has been found that the new pyrimidyl-thio-carboxanilides of the formula (I) have herbicidal properties, particularly also selective herbicidal properties.

Surprisingly, the pyrimidyl-thio-carboxanilides of the formula (I) demonstrate significantly better herbicidal properties than previously known, constitutionally similar substances of the same mode of action.

DETAILED DESCRIPTION OF THE INVENTION

The pyrimidyl-thio-carboxanilides according to the invention are defined by the formula (I). Compounds of the formula (I)

in which

R¹ represents hydrogen, fluorine, chlorine, bromine, in each case straight-chain or branched C₁ to C₄ alkyl, straight-chain or branched C₁ to C₄ alkoxy or straight-chain or branched C₁ to C₄ alkylthio or trifluoromethyl, R² represents hydrogen, fluorine, chlorine, bromine, straight-chain or branched alkyl having 1 to 4 carbon atoms or trifluoromethyl, R³ represents fluorine, chlorine, bromine, methyl or methoxy, n represents an integer 0, 1 or 2 and Z represents the radical

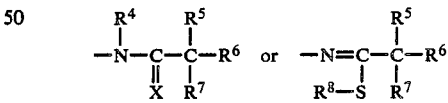

where

X represents oxygen or sulphur,

R⁴ represents hydrogen, hydroxyl, in each case straight-chain or branched C₁ to C₄ alkyl or C₁ to C₄ alkoxy, in each case straight-chain or branched C₃ to C₄ alkenyl or C₃ to C₄ alkynyl, with the proviso that R⁴ does not represent hydrogen when X represents oxygen, R⁵ represents hydrogen, fluorine, chlorine, bromine or straight-chain or branched alkyl having 1 to 4 carbon atoms which is unsubstituted or mono- to nona-substituted, identically or differently, by fluorine, chlorine or bromine, or R⁴ and R⁵, together with the carbon atom or the nitrogen atom to which they are bonded, form a 3- to 8-membered heterocyclic ring which is unsubstituted or mono- to dodeca-substituted, identically or differently, by methyl or ethyl and which may contain one, two, three or four double bonds, $R^6$ and $R^7$, independently of one another, represent fluorine, chlorine, bromine or straight-chain or branched alkyl having 1 to 4 carbon atoms which is unsubstituted or mono- to nona-substituted, identically or differently, by fluorine and chlorine, or $R^6$ and $R^7$, together with the carbon atom to which they are bonded, form a 3- to 8-membered ring which contains, if appropriate, 1 or 2 oxygen and/or sulphur atoms as ring members in addition to carbon and which is unsubstituted or mono- to dodeca-substituted, identically or differently, by fluorine, chlorine, methyl or ethyl and which may contain one or two double bonds, and $R^8$ represents hydrogen, straight-chain or branched alkyl having 1 to 4 carbon atoms which is optionally singly to quintuply, identically or differently substituted by fluorine or chlorine, or in each case straight-chain or branched $C_3$ to $C_6$ alkenyl or $C_3$ to $C_6$ alkynyl, are preferred.

Compounds of the formula (I) in which $R^1$ represents hydrogen, fluorine, chlorine, bromine, methyl, ethyl, methoxy, ethoxy, methylthio, ethylthio or trifluoromethyl, $R^2$ represents hydrogen, fluorine, chlorine, bromine, methyl, ethyl or trifluoromethyl, $R^3$ represents fluorine, chlorine, bromine, methyl or methoxy, n represents an integer 0, 1 or 2, Z represents the radical

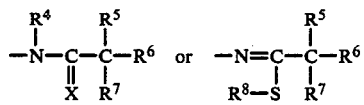

where

X represents oxygen or sulphur, $R^4$ represents hydrogen, hydroxyl, methyl, ethyl, methoxy, ethoxy, allyl or propargyl, with the proviso that $R^4$ does not represent hydrogen when X represents oxygen, $R^5$ represents hydrogen, fluorine, chlorine, bromine, methyl or ethyl, or $R^4$ and $R^5$, together with the carbon atom or the nitrogen atom to which they are bonded, form a 3- to 8-membered heterocyclic ring which is unsubstituted or mono- to hexa-substituted, identically or differently, by methyl or ethyl, $R^6$ and $R^7$, independently of one another, represent fluorine, chlorine, bromine, methyl, ethyl or isopropyl, or $R^6$ and $R^7$, together with the carbon atom to which they are bonded, form a 3- to 8-membered ring which, if appropriate, contains 1 or 2 oxygen and/or sulphur atoms as ring members in addition to carbon and which is optionally singly to triply, identically or differently, substituted by fluorine, chlorine, methyl or ethyl, $R^8$ represents hydrogen, or methyl, ethyl, or iso-propyl, which are optionally singly to quintuply, identically or differently substituted by fluorine or chlorine, allyl or propargyl, are particularly preferred.

In detail, the following pyrimidyl-thio-carboxanilides of the formula (I) may be mentioned apart from the compounds mentioned in the preparation examples:

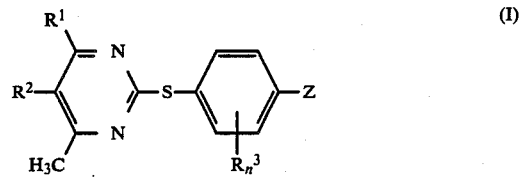

(I)

TABLE 1

$$Z = -N-C-C-R^6$$
with $R^4$, $R^5$, $R^7$, and $X$ substituents

| $R^1$ | $R^2$ | $R^3$ | $R^4$ | $R^5$ | $R^6$ | $R^7$ | X |
|---|---|---|---|---|---|---|---|
| CH₃ | H | H | C₂H₅ | CH₃ | CH₃ | CH₃ | O |
| CH₃ | H | H | i-C₃H₇ | CH₃ | CH₃ | CH₃ | O |
| CH₃ | H | H | CH₂—CH=CH₂ | CH₃ | CH₃ | CH₃ | O |
| CH₃ | H | H | CH₂—C≡CH | CH₃ | CH₃ | CH₃ | O |
| CH₃ | H | H | —(CH₂)₄— | | CH₃ | CH₃ | O |
| CH₃ | H | H | —(CH₂)₃— | | CH₃ | CH₃ | O |
| CH₃ | H | H | CH₃ | CH₃ | CH₃ | H | O |
| CH₃ | H | H | CH₃ | C₂H₅ | C₂H₅ | H | O |
| CH₃ | H | Cl | CH₃ | CH₃ | CH₃ | CH₃ | O |
| CH₃ | H | Cl | —CH₂—CH=CH₂ | CH₃ | CH₃ | CH₃ | O |
| CH₃ | H | Cl | —(CH₂)₃— | | H | H | O |
| CH₃ | H | Cl | —(CH₂)₃— | | CH₃ | CH₃ | O |
| CH₃ | H | Cl | —(CH₂)₄— | | H | H | O |
| CH₃ | H | Cl | —(CH₂)₄— | | CH₃ | CH₃ | O |
| CH₃ | H | Cl | CH₃ | CH₃ | CH₃ | H | O |
| CH₃ | H | Cl | —CH₂—CH=CH₂ | CH₃ | CH₃ | H | O |
| CH₃ | H | Cl | CH₃ | C₂H₅ | C₂H₅ | H | O |
| H | C₂H₅ | Cl | CH₃ | CH₃ | CH₃ | CH₃ | O |
| H | C₂H₅ | CH₃ | —(CH₂)₃— | | CH₃ | CH₃ | O |
| H | C₂H₅ | OCH₃ | —CH₂—CH=CH₂ | CH₃ | CH₃ | CH₃ | O |
| H | H | H | CH₃ | CH₃ | CH₃ | CH₃ | O |
| H | H | H | —(CH₂)₃— | | CH₃ | CH₃ | O |
| H | H | H | —CH₂—CH=CH₂ | C₂H₅ | C₂H₅ | H | O |
| H | H | Cl | CH₃ | CH₃ | CH₃ | CH₃ | O |

TABLE 1-continued $$Z = -N\overset{R^4}{\underset{\underset{X}{\|}}{C}}-\overset{R^5}{\underset{R^7}{C}}-R^6$$

| R¹ | R² | R³ | R⁴ | R⁵ | R⁶ | R⁷ | X |
|---|---|---|---|---|---|---|---|
| H | H | CH₃ | —(CH₂)₄— | | CH₃ | CH₃ | O |
| H | H | OCH₃ | —CH₂—CH=CH₂ | CH₃ | CH₃ | H | O |
| CH₃ | Cl | H | CH₃ | CH₃ | CH₃ | CH₃ | O |
| CH₃ | Cl | H | —(CH₂)₃— | | CH₃ | CH₃ | O |
| CH₃ | Cl | Cl | CH₃ | CH₃ | CH₃ | CH₃ | O |
| CH₃ | H | H | H | CH₃ | CH₃ | i-C₃H₇ | S |
| CH₃ | H | H | H | CH₃ | —(CH₂)₄— | | S |
| CH₃ | H | H | —(CH₂)₄— | CH₃ | CH₃ | CH₃ | S |
| CH₃ | H | Cl | H | CH₃ | CH₃ | CH₃ | S |
| CH₃ | H | H | H | CH₃ | —(CH₂)₅— | H | S |
| CH₃ | H | OCH₃ | CH₃ | C₂H₅ | C₂H₅ | H | O |
| CH₃ | H | OCH₃ | —CH₂—CH=CH₂ | C₂H₅ | C₂H₅ | H | O |
| CH₃ | CH₃ | H | CH₃ | CH₃ | CH₃ | CH₃ | O |
| CH₃ | CH₃ | H | —CH₂—CH=CH₂ | CH₃ | CH₃ | CH₃ | O |
| CH₃ | CH₃ | H | —(CH₂)₃— | | CH₃ | CH₃ | O |
| CH₃ | CH₃ | Cl | CH₃ | CH₃ | CH₃ | CH₃ | O |
| CH₃ | CH₃ | CH₃ | —(CH₂)₃— | | CH₃ | CH₃ | O |
| CH₃ | CH₃ | H | —CH₂—CH=CH₂ | CH₃ | CH₃ | CH₃ | O |
| CH₃ | H | CH₃ | CH₃ | CH₃ | CH₃ | CH₃ | O |
| CH₃ | H | CH₃ | —CH₂—CH=CH₂ | CH₃ | CH₃ | CH₃ | O |
| CH₃ | H | CH₃ | —(CH₂)₃— | | CH₃ | CH₃ | O |
| CH₃ | H | CH₃ | —(CH₂)₄— | | CH₃ | CH₃ | O |
| CH₃ | H | CH₃ | —CH₃ | CH₃ | CH₃ | H | O |
| CH₃ | H | CH₃ | —CH₂—CH=CH₂ | CH₃ | CH₃ | H | O |
| CH₃ | H | CH₃ | —CH₃ | C₂H₅ | C₂H₅ | H | O |
| CH₃ | H | CH₃ | —CH₂—CH=CH₂ | C₂H₅ | C₂H₅ | H | O |
| CH₃ | H | OCH₃ | CH₃ | CH₃ | CH₃ | CH₃ | O |
| CH₃ | H | OCH₃ | —CH₂CH=CH₂ | CH₃ | CH₃ | CH₃ | O |
| CH₃ | H | OCH₃ | —(CH₂)₃— | | CH₃ | CH₃ | O |
| CH₃ | H | OCH₃ | —(CH₂)₄— | | CH₃ | CH₃ | O |
| CH₃ | H | OCH₃ | CH₃ | CH₃ | CH₃ | H | O |
| CH₃ | H | OCH₃ | —CH₂—CH=CH₂ | CH₃ | CH₃ | H | O |
| CH₃ | H | OCH₃ | CH₃ | C₂H₅ | C₂H₅ | H | O |
| CH₃ | H | OCH₃ | —CH₂—CH=CH₂ | C₂H₅ | C₂H₅ | H | O |
| CH₃ | CH₃ | H | CH₃ | CH₃ | CH₃ | CH₃ | O |
| CH₃ | CH₃ | H | —CH₂—CH=CH₂ | CH₃ | CH₃ | CH₃ | O |
| CH₃ | CH₃ | H | —(CH₂)₃— | | CH₃ | CH₃ | O |
| CH₃ | CH₃ | Cl | CH₃ | CH₃ | CH₃ | CH₃ | O |
| CH₃ | CH₃ | CH₃ | —(CH₂)₃— | | CH₃ | CH₃ | O |
| CH₃ | CH₃ | OCH₃ | —CH₂—CH=CH₂ | CH₃ | CH₃ | CH₃ | O |
| H | C₂H₅ | H | CH₃ | CH₃ | CH₃ | CH₃ | O |
| H | C₂H₅ | H | —(CH₂)₃— | | CH₃ | CH₃ | O |
| H | C₂H₅ | H | —CH₂—CH=CH₂ | CH₃ | CH₃ | H | O |
| CH₃ | H | Cl | CH₃ | CH₃ | CH₃ | H | O |
| CH₃ | H | Cl | —CH₂—CH=CH₂ | CH₃ | CH₃ | H | O |
| CH₃ | H | Cl | CH₃ | C₂H₅ | C₂H₅ | H | O |
| CH₃ | H | CH₃ | CH₃ | CH₃ | CH₃ | CH₃ | O |
| CH₃ | H | CH₃ | —CH₂—CH=CH₂ | CH₃ | CH₃ | CH₃ | O |
| CH₃ | H | CH₃ | —(CH₂)₃— | | CH₃ | CH₃ | O |
| CH₃ | H | CH₃ | —(CH₂)₄— | | CH₃ | CH₃ | O |
| CH₃ | H | CH₃ | CH₃ | CH₃ | CH₃ | H | O |
| CH₃ | H | CH₃ | —CH₂—CH=CH₂ | CH₃ | CH₃ | H | O |
| CH₃ | H | CH₃ | —CH₃ | C₂H₅ | C₂H₅ | H | O |
| CH₃ | H | CH₃ | —CH₂—CH=CH₂ | C₂H₅ | C₂H₅ | H | O |
| CH₃ | H | OCH₃ | CH₃ | CH₃ | CH₃ | CH₃ | O |
| CH₃ | H | OCH₃ | —CH₂CH=CH₂ | CH₃ | CH₃ | CH₃ | O |
| CH₃ | H | OCH₃ | —(CH₂)₃— | | CH₃ | CH₃ | O |
| CH₃ | H | OCH₃ | —(CH₂)₄— | | CH₃ | CH₃ | O |
| CH₃ | H | OCH₃ | CH₃ | CH₃ | CH₃ | H | O |
| CH₃ | H | OCH₃ | —CH₂—CH=CH₂ | CH₃ | CH₃ | H | O |
| CH₃ | H | Cl | H | CH₃ | CH₃ | i-C₃H₇ | S |
| CH₃ | H | Cl | H | CH₃ | CH₃ | —CH=CH₂ | S |
| CH₃ | H | Cl | H | CH₃ | —(CH₂)₄— | | S |
| CH₃ | H | Cl | —(CH₂)₃— | | CH₃ | CH₃ | S |
| CH₃ | H | CH₃ | H | CH₃ | CH₃ | CH₃ | S |
| CH₃ | H | CH₃ | H | CH₃ | CH₃ | i-C₃H₇ | S |
| CH₃ | H | CH₃ | H | CH₃ | CH₃ | —CH=CH₂ | S |
| CH₃ | H | CH₃ | H | CH₃ | —CH₂)₄— | | S |
| CH₃ | H | CH₃ | —(CH₂)₃ | | CH₃ | CH₃ | S |
| CH₃ | H | OCH₃ | H | CH₃ | CH₃ | CH₃ | S |
| CH₃ | H | OCH₃ | H | CH₃ | CH₃ | i-C₃H₇ | S |
| CH₃ | H | OCH₃ | H | CH₃ | CH₃ | —CH=CH₂ | S |
| CH₃ | H | OCH₃ | H | CH₃ | —(CH₂)₄— | | S |
| CH₃ | H | OCH₃ | —(CH₂)₃ | | CH₃ | CH₃ | S |
| CH₃ | CH₃ | H | H | CH₃ | CH₃ | CH₃ | S |

TABLE 1-continued $$Z = -\underset{\underset{X}{\|}}{N}-\underset{R^7}{\overset{R^4}{C}}-\underset{R^7}{\overset{R^5}{C}}-R^6$$

| R¹ | R² | R³ | R⁴ | | R⁵ | R⁶ | R⁷ | X |
|---|---|---|---|---|---|---|---|---|
| CH₃ | CH₃ | H | H | | CH₃ | CH₃ | i-C₃H₇ | S |
| CH₃ | CH₃ | H | H | | CH₃ | CH₃ | —CH=CH₂ | S |
| CH₃ | CH₃ | H | H | | CH₃ | —(CH₂)₄— | | S |
| CH₃ | CH₃ | H | —(CH₂)₃— | | CH₃ | CH₃ | CH₃ | S |
| H | C₂H₅ | H | H | | CH₃ | CH₃ | CH₃ | S |
| H | C₂H₅ | H | H | | CH₃ | CH₃ | i-C₃H₇ | S |
| H | C₂H₅ | H | H | | CH₃ | CH₃ | —CH=CH₂ | S |
| H | C₂H₅ | H | H | | CH₃ | —(CH₂)₄— | | S |
| H | C₂H₅ | H | —(CH₂)₃— | | CH₃ | CH₃ | CH₃ | S |
| H | H | H | H | | CH₃ | CH₃ | CH₃ | S |
| H | H | H | H | | CH₃ | CH₃ | i-C₃H₇ | S |
| H | H | H | H | | CH₃ | CH₃ | —CH=CH₂ | S |
| H | H | H | H | | CH₃ | —(CH₂)₄— | | S |
| H | H | H | —(CH₂)₃— | | CH₃ | CH₃ | CH₃ | S |
| CH₃ | Cl | | H | | CH₃ | CH₃ | CH₃ | S |
| CH₃ | Cl | | H | | CH₃ | CH₃ | CH₃ | S |
| CH₃ | Cl | | H | | CH₃ | CH₃ | CH₃ | S |
| CH₃ | Cl | H | H | | CH₃ | —(CH₂)₄— | | S |
| CH₃ | Cl | | —(CH₂)₃ | | CH₃ | CH₃ | | S |

TABLE 2

$$Z = -N=\underset{R^8-S}{\overset{}{C}}-\underset{R^7}{\overset{R^5}{C}}-R^6$$

| R¹ | R² | R³ | R⁵ | R⁶ | R⁷ | R⁸ |
|---|---|---|---|---|---|---|
| CH₃ | H | H | CH₃ | CH₃ | CH₃ | CH₃ |
| CH₃ | H | H | CH₃ | CH₃ | CH₃ | C₂H₅ |
| CH₃ | H | H | CH₃ | CH₃ | CH₃ | i-C₃H₇ |
| CH₃ | H | H | CH₃ | CH₃ | CH₃ | CH₂—CH=CH₂ |
| CH₃ | H | H | CH₃ | CH₃ | CH₃ | CH₂—C≡CH |
| CH₃ | H | H | CH₃ | CH₃ | i-C₃H₇ | CH₃ |
| CH₃ | H | H | CH₃ | CH₃ | —CH=CH₂ | CH₃ |
| CH₃ | H | H | CH₃ | CH₃ | i-C₃H₇ | i-C₃H₇ |
| CH₃ | H | H | CH₃ | CH₃ | —CH=CH₂ | i-C₃H₇ |
| CH₃ | H | H | CH₃ | CH₃ | i-C₃H₇ | CH₂—CH=CH₂ |
| CH₃ | H | H | CH₃ | CH₃ | —CH=CH₂ | CH₂—CH=CH₂ |
| CH₃ | H | H | CH₃ | CH₃ | i-C₃H₇ | CH₂—C≡CH |
| CH₃ | H | H | CH₃ | CH₃ | —CH=CH₂ | CH₂—C≡CH |
| CH₃ | H | Cl | CH₃ | CH₃ | CH₃ | CH₃ |
| CH₃ | H | Cl | CH₃ | CH₃ | CH₃ | i-C₃H₇ |
| CH₃ | H | Cl | CH₃ | CH₃ | CH₃ | CH₂—CH=CH₂ |
| CH₃ | H | CH₃ | CH₃ | CH₃ | CH₃ | CH₃ |
| CH₃ | H | CH₃ | CH₃ | CH₃ | CH₃ | i-C₃H₇ |
| CH₃ | H | CH₃ | CH₃ | CH₃ | CH₃ | CH₂—CH=CH₂ |
| CH₃ | H | OCH₃ | CH₃ | CH₃ | CH₃ | CH₃ |
| CH₃ | H | OCH₃ | CH₃ | CH₃ | CH₃ | i-C₃H₇ |
| CH₃ | H | OCH₃ | CH₃ | CH₃ | CH₃ | CH₂—CH=CH₂ |
| CH₃ | CH₃ | H | CH₃ | CH₃ | CH₃ | CH₃ |
| CH₃ | CH₃ | H | CH₃ | CH₃ | CH₃ | i-C₃H₅ |
| CH₃ | CH₃ | H | CH₃ | CH₃ | CH₃ | CH₂—CH=CH₂ |
| CH₃ | CH₃ | Cl | CH₃ | CH₃ | CH₃ | CH₃ |
| CH₃ | CH₃ | Cl | CH₃ | CH₃ | CH₃ | i-C₃H₇ |
| CH₃ | CH₃ | Cl | CH₃ | CH₃ | CH₃ | CH₂CH=CH₂ |
| CH₃ | CH₃ | CH₃ | CH₃ | CH₃ | CH₃ | CH₃ |
| CH₃ | CH₃ | CH₃ | CH₃ | CH₃ | CH₃ | i-C₃H₇ |
| CH₃ | CH₃ | CH₃ | CH₃ | CH₃ | CH₃ | CH₂—CH=CH₂ |
| CH₃ | CH₃ | OCH₃ | CH₃ | CH₃ | CH₃ | CH₃ |
| CH₃ | CH₃ | OCH₃ | CH₃ | CH₃ | CH₃ | i-C₃H₇ |
| CH₃ | CH₃ | OCH₃ | CH₃ | CH₃ | CH₃ | —CH₂—CH=CH₂ |
| H | C₂H₅ | H | CH₃ | CH₃ | CH₃ | CH₃ |
| H | C₂H₅ | H | CH₃ | CH₃ | CH₃ | i-C₃H₇ |
| H | C₂H₅ | H | CH₃ | CH₃ | CH₃ | —CH₂—CH=CH₂ |
| H | C₂H₅ | Cl | CH₃ | CH₃ | CH₃ | CH₃ |
| H | C₂H₅ | CH₃ | CH₃ | CH₃ | CH₃ | CH₃ |
| H | C₂H₅ | OCH₃ | CH₃ | CH₃ | CH₃ | CH₃ |
| H | H | H | CH₃ | CH₃ | CH₃ | CH₃ |
| H | H | H | CH₃ | CH₃ | CH₃ | i-C₃H₇ |
| H | H | H | CH₃ | CH₃ | CH₃ | —CH₂CH=CH₂ |
| CH₃ | Cl | H | CH₃ | CH₃ | CH₃ | CH₃ |

TABLE 2-continued $$Z = -N=C-C-R^6 \atop R^8-S \; R^7 \; \overset{R^5}{|}$$

| R¹ | R² | R³ | R⁵ | R⁶ | R⁷ | R⁸ |
|---|---|---|---|---|---|---|
| CH₃ | Cl | H | CH₃ | CH₃ | CH₃ | i-C₃H₇ |

If, for example, 4-[(4,6-dimethyl-2-mercapto)-pyrimidyl]-N-methyl-aniline and pivaloyl chloride are used as starting materials, the course of the reaction of the process (a-α) according to the invention can then be represented by the following scheme:

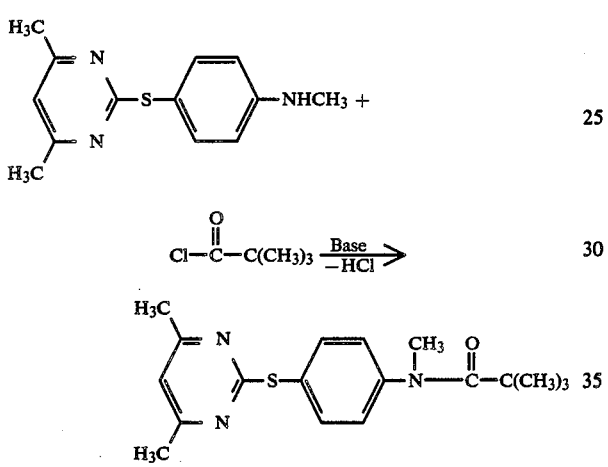

If, for example, 4-[(4,6-dimethyl-2-mercapto)-pyrimidyl]-(2-ethylbutyr)-anilide and alkyl bromide are used as starting materials, the course of the reaction of the process (a-β) according to the invention can then be represented by the following scheme:

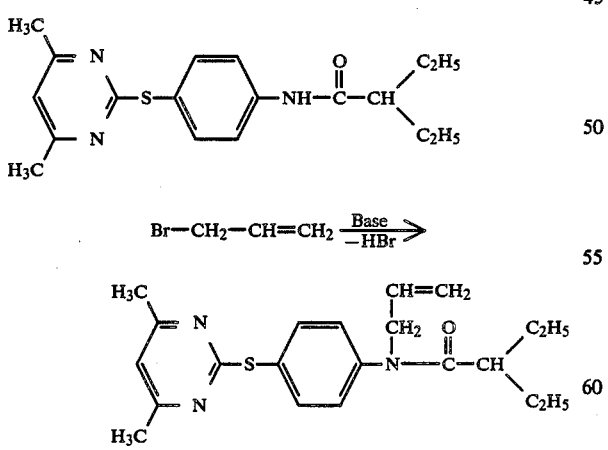

If, for example, 4-[(4,6-dimethyl-2-mercapto)-pyrimidyl]-pivaloylanilide and the the Lawesson reagent are used as starting materials, the course of the reaction of the process (b) according to the invention can then be represented by the following scheme:

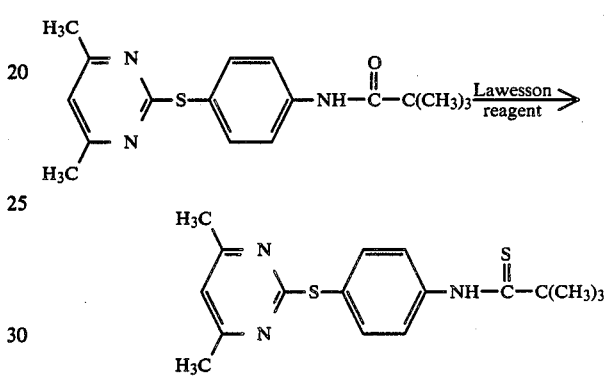

If, for example, 4-[(4,6-dimethyl-2-mercapto)-pyrimidyl]-pivaloylthioanilide and methyl iodide are used as starting materials, the course of the reaction of the process (c) according to the invention can then be represented by the following scheme:

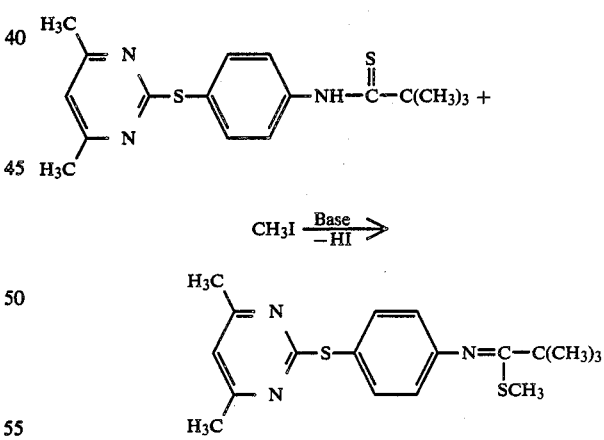

The 4-(pyrimidyl-thio)-anilines required as starting materials in the process (a-α) according to the invention are generally defined by the formula (II). In the formula (II), R¹, R², R³, R⁴ and n preferably have the meanings which have already been mentioned as being preferable for these radicals and this index, respectively, in connection with the description of the substances of the formula (I) according to the invention.

Some of the 4-(pyrimidyl-thio)-anilines of the formula (II) are known. They can be prepared by (d) reacting pyrimidine derivatives of the formula (VI)

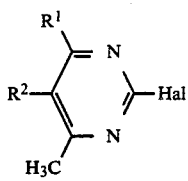

in which
R¹ and R² have the abovementioned meaning and
Hal represents halogen
with 4-amino-thiophenols of the formula

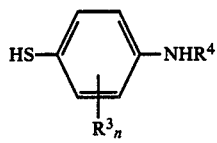

in which R³, R⁴ and n have the abovementioned meaning, if appropriate in the presence of an acid binder and if appropriate in the presence of a diluent, or (e) reducing 2-(4-nitro-thiophenoxy)-pyrimidine derivatives of the formula (VIII),

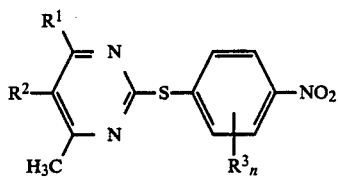

in which R¹, R², R³ and n have the abovementioned meaning, by conventional methods, if appropriate in the presence of a diluent.

The pyrimidine derivatives required as starting materials in the process (d) above are defined by the formula (VI). In this formula, R¹ and R² preferably have the meanings which have already been mentioned as being preferable for these radicals in connection with the description of the substances of the formula (I) according to the invention. Hal preferably represents fluorine, chlorine or bromine.

The pyrimidine derivatives of the formula (VI) are known or can be prepared in a simple manner according to methods which are known in principle. Thus, pyrimidine derivatives of the formula (VI) can be obtained, for example, by reacting 2-hydroxy-pyrimidine derivatives (dihydro-pyrimidone-2 derivatives) with inorganic acid halides, such as, for example, phosphoroxy chloride or phosphorus pentachloride, or alternatively by reacting appropriate 2-amino-pyrimidine derivatives with nitric acid in the presence of hydrohalic acids.

The 4-amino-thiophenols which are furthermore required as starting materials in the process (d) are defined by the formula (VII). In this formula, R³, R⁴ and n preferably have the meanings which have already been mentioned as being preferable for these radicals and for this index, respectively, in connection with the description of the substances of the formula (I) according to the invention.

The 4-amino-thiopheols of the formula (VII) are known or can be prepared in a simple manner according to methods which are known in principle.

All acid acceptors which can be used conventionally for this type of reaction can be used as acid binders when process (d) is carried out. Alkali metal and alkaline earth metal oxides, hydroxides and carbonates, such as sodium hydroxide, potassium hydroxide, calcium oxide, sodium carbonate and potassium carbonate, furthermore alkali metal alcoholates, amides and hydrides, such as, for example, sodium methylate, sodium ethylate, potassium tert.-butylate, sodium amide and sodium hydride, can preferably be used.

All conventional inert organic solvents can be used as diluents when the process (d) is carried out. Preferably suitable are hydrocarbons, such as benzene, toluene and xylene, furthermore ethers such as dioxane, glycol dimethyl ether and diglycol dimethyl ether, in addition nitriles, such as acetonitrile, and also strongly polar solvents, such as dimethyl sulphoxide, sulpholane and dimethylformamide.

The reaction temperatures can be varied within a relatively wide range when the process (d) is carried out. In general, the reaction is carried out at temperatures between 0° C. and 200° C., preferably between 50° C. and 150° C.

The reaction according to the process (d) is, in general, carried out under standard pressure.

In general, the starting materials of the formulae (VI) and (VII) are reacted in approximately equimolar amounts when the process (d) is carried out. It is, however, also possible to use one or other of the components in a relatively large excess. Work-up occurs according to conventional methods.

The 2-(4-nitro-thiophenoxy)-pyrimidine derivatives which are required as starting materials in the process (e) are defined by the formula (VIII). In this formula, R¹, R², R³ and n preferably have the meanings which have already been mentioned as being preferable for these radicals and for this index, respectively, in connection with the description of the substances of the formula (I) according to the invention.

The compounds of the formula (VIII) are known or can be prepared in a simple manner according to methods which are known in principle. Thus, compounds of the formula (VIII) are obtained, for example, by reacting pyrimidine derivatives of the formula (VI),

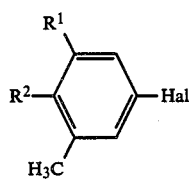

in which R¹, R² and Hal have the abovementioned meaning, with 4-nitro-thiophenols of the formula (IX),

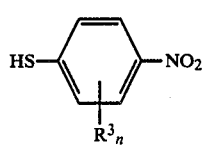

in which R³ and n have the abovementioned meaning, in the presence of an acid binder and if appropriate in the presence of a diluent at temperatures between 0° C. and 200° C., preferably between 50° C. and 150° C. Suitable acid binders and diluents here are preferably the substances which have already been mentioned as being those acid acceptors and solvents which can be preferably used in connection with the process (d).

Suitable reducing agents in the process (e) are all the substances which are conventionally employed for the reduction of aromatic nitro compounds. Elementary metals, such as iron, zinc and tin, furthermore metal compounds in low valency states, such as iron(II) and tin(II) salts, and, in addition, non-metallic compounds in lower valency states, such as, for example, salts of hydrogen sulphide, and also alkali metal sulphites and alkali metal dithionites can preferably be used. As well as this, the reduction can also be carried out by means of catalytic hydrogenation using hydrogen in the presence of a catalyst, such as, for example, Raney nickel.

Suitable diluents in the process (e) are all conventional organic solvents which are suitable for this type of reduction. The reaction temperatures can be varied within a relatively wide range. They correspond to the temperatures which are used in analogous reactions.

The reduction according to the process (e) is carried out and the reaction mixture which is produced is worked up according to conventional methods.

The carboxylic acid derivatives which are required as reaction components in the process (a, version $\alpha$) according to the invention are unambiguously defined by the formula (III). In this formula, $R^5$, $R^6$ and $R^7$ preferably have the meanings which have already been mentioned as being preferable for these radicals in connection with the description of the substances of the formula (I) according to the invention. Y preferably represents fluorine, chlorine, bromine, benzenesulphonyl or toluene-sulphonyl.

The acid halides of the formula (III) are known or can be prepared in a simple fashion according to methods which are known in principle.

Suitable acid binders in the reaction according to the process (a, version $\alpha$) according to the invention are all conventional acid acceptors. Tertiary amines, such as triethylamine, pyridine and N-N-dimethyl-aniline, furthermore alkaline earth metal oxides, such as magnesium oxide and calcium oxide, in addition alkali metal carbonates and alkaline earth metal carbonates, such as sodium carbonate, potassium carbonate and calcium carbonate, can preferably be used. It is also possible to use the respective aniline derivatives of the formula (II) simultaneously as acid binders. For this purpose, the aniline compound concerned must then be employed at least in such an amount that the liberated hydrogen halide can be bound.

All solvents which are inert towards acid halides can be employed as diluents in the process (a, version $\alpha$) according to the invention. Hydrocarbons, such as benzine, benzene, toluene, xylene and tetraline, in addition ketones, such as acetone and methyl isopropyl ketone, furthermore ethers, such as diethyl ether, tetrahydrofuran and dioxane, moreover carboxylic acid esters, such as ethyl acetate, and also strongly polar solvents, such as dimethyl sulphoxide and sulpholane, can preferably be used. If the stability to hydrolysis of the acid halide allows, the reaction can also be carried out in the presence of water.

The reaction temperatures can be varied within a relatively wide range when the process (a, version $\alpha$) according to the invention is carried out. If the reaction is carried out without solvent and acid binder, then, in general, the components are initially allowed to react at temperatures between $-20°$ C. and $+20°$ C. and then they are heated to temperatures between $70°$ and $200°$ C. If the reaction is carried out in the presence of a diluent and an acid binder, then the reaction temperatures are in general between $-20°$ C. and $+100°$ C., preferably between $0°$ C. and $50°$ C.

The process (a, version $\alpha$) according to the invention is, in general, carried out under standard pressure.

The starting materials of the formulae (II) and (III) are, in general, used in approximately equivalent amounts when the process (a, version $\alpha$) according to the invention is carried out. However, it is also possible to employ one or other of the components in a relatively large excess. The work-up occurs according to conventional methods. In general, precipitated salts are removed and the reaction mixture which remains is concentrated by stripping off the diluent. If the reaction is carried out in the presence of water or water-miscible solvents, then the reaction mixture can also be diluted with water, the mixture produced filtered under suction or extracted with a sparingly water-soluble organic solvent, the organic phase is washed and concentrated, and the residue which remains subjected, if appropriate, to conventional purification processes.

The pyrimidyl-thio-carboxanilides which are required as starting materials in the process (a, version $\beta$) according to the invention are generally defined by the formula (Ia-1). In this formula, $R^1$, $R^2$, $R^3$, $R^5$, $R^6$, $R^7$ and n preferably have the meanings which have already been mentioned as being preferable for these radicals in connection with the description of the substances of the formula (I) according to the invention.

The compounds of the formula (Ia-1) are substances according to the invention and can be obtained according to process (a/version $\alpha$).

The alkylating agents furthermore required for carrying out the process (a/version $\beta$) according to the invention are generally defined by the formula (IV).

In the formula (IV), $R^4$ preferably has the meaning which has already been mentioned as being preferable for this radical in connection with the description of the substances according to the invention, and U preferably represents chlorine or bromine.

The alkylating agents of the formula (IV) are generally known compounds of organic chemistry.

The diluents which are also preferably suitable in the process (a, version $\alpha$) can also preferably be used as diluents when the process (a, version $\beta$) according to the invention is carried out.

The reaction temperatures can also be varied within a relatively wide range in the process (a, version $\beta$) according to the invention. In general, the reaction is carried out at temperatures between $-20°$ C. and $+150°$ C., preferably between $0°$ and $100°$ C.

The process (a, version $\beta$) according to the invention is, in general, carried out under standard pressure.

The starting materials of the formulae (Ia-1) and (IV) are, in general, used in approximately equivalent amounts when the process (a, version $\beta$) according to the invention is carried out. However, it is also possible to employ the alkylating agent in a relatively large excess. The work-up occurs according to conventional methods.

The pyrimidyl-thio-carboxanilides which are required as starting materials for carrying out the process (b) according to the invention are generally defined by the formula (Ia). In the formula (Ia), $R^1$, $R^2$, $R^3$, $R^4$, $R^5$, $R^6$, $R^7$ and n preferably represent the meanings which have already been mentioned as being preferable for these radicals in connection with the description of the substances of the formula (I) according to the invention.

The pyrimidyl-thio-carboxanilides of the formula (Ia) are compounds according to the invention and can be obtained according to processes (a/versions α and β).

In the process (b) according to the invention, $P_4S_{10}$ and 2,4-bis-(4-methoxyphenyl)-2,4-dithiono-1,3,2,4-dithiodiphosphetane (Lawesson reagent) are preferably used as sulphurizing agents. The sulphurizing agents are known compounds.

All solvents which are conventional for these types of reactions can be employed as diluents in the process (b) according to the invention. Hydrocarbons, such as toluene, xylene or benzene, are preferably used.

The reaction temperatures can be varied within a relatively wide range in the process (b) according to the invention. In general, the reaction is carried out at temperatures between +20° C. and 200° C., preferably at the corresponding boiling temperature of the solvent used.

The pyrimidyl-thio-carboxanilides which are required as starting materials for carrying out the process (c) according to the invention are generally defined by the formula (Ib). In this formula, $R^1$, $R^2$, $R^3$, $R^4$, $R^5$, $R^6$, $R^7$ and n preferably have for the meanings which have already been mentioned as being preferable for these radicals in connection with the description of the substances of the formula (I) according to the invention.

The pyrimidyl-thio-carboxanilides of the formula (Ib) are compounds according to the invention and can be obtained according to process (b).

The alkylating agents which are furthermore required for carrying out the process (c) according to the invention are generally defined by the formula (V). In the formula (V), $R^8$ preferably has the meaning which has already been mentioned as being preferable for this radical in connection with the description of the substances of the formula (I) according to the invention, and U preferably represents chlorine or bromine.

The alkylating agents of the formula (V) are known compounds of organic chemistry.

The diluents and acid binders which are also used in the presence (a/version β) are preferably used as diluents and acid binders when the process (c) according to the invention is carried out.

The reaction temperatures can be varied within a relatively wide range when the process (c) according to the invention is carried out. In general, the reaction is carried out at temperatures between −20° C. and +150° C., preferably between 0° and 100° C.

The starting materials of the formulae (I) and (V) are, in general, used in approximately equivalent amounts when the process (c) according to the invention is carried out. However, it is also possible to employ the alkylating agent of the formula (V) in a relatively large excess. The work-up occurs according to conventional methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Circium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4-(1H,3H)-dione or N-(2-benzothiazolyl)-N,N'-dimethyl-urea for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soya beans. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

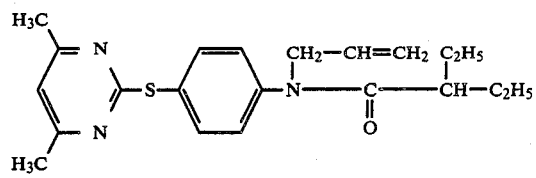

Process (a-β)

6.6 g (20 mmol) of 4-[4,6-dimethyl-2-mercato)-pyrimidyl]-(2-ethyl-butyr)-anilide in 50 ml of absolute dimethylformamide are added dropwise to 0.75 g (25 mmol) of sodium hydride in 20 ml of absolute dimethylformamide at room temperature. When hydrogen evolution has ended, 2.2 ml (25 mmol) of allyl bromide are added and the reaction mixture is stirred at room temperature, checks being made by thin layer chromatography. After dropwise addition of a little ice water, the reaction mixture is poured into water. The reaction product is subsequently extracted with methylene chloride and dried by means of sodium sulphate, and the solvent is distilled off in vacuo.

After column chromatography using cyclohexane/ethyl acetate (2:1), 3.62 g (49% of theory) of 4-[4,6-dimethyl-2-mercapto)-pyrimidyl]-N-allyl-(2-ethyl-butyr)-anilide of melting point 97°–98° C. are obtained.

Example 2

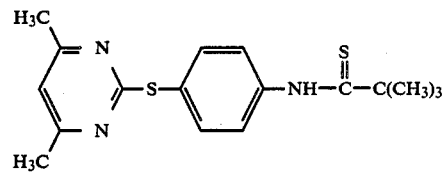

Process (b)

9.5 g (30 mmol) of 4-[(4,6-dimethyl-2-mercaptopyrimidyl]-pivaloylanilide and 6.6 g (16.5 mmol) of Lawesson reagent (2,4-bis-(4-methoxyphenyl)-2,4-dithiono-1,3,2,4-dithiaphosphetan) are refluxed for 3 hours in 30 ml of absolute toluene. After cooling to room temperature, the reaction mixture is chromatographed using cyclohexane/ethyl acetate (2:1).

4.55 g (46% of theory) of 4-[(4,6-dimethyl-2-mercapto)-pyrimidyl]-pivaloylthioanilide of melting point 165°–167° C. are obtained.

Example 3

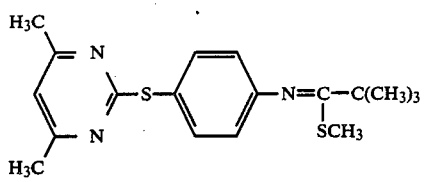

Process (c)

6.62 g (20 mmol) of 4-[(4,6-dimethyl-2-mercaptopyrimidyl]-pivaloylthioanilide in 30 ml of absolute dimethylformamide are added dropwise to 0.9 g (30 mmol) of sodium hydride in 20 ml of absolute dimethylformamide under a nitrogen atmosphere. When the evolution of hydrogen has ended, 2.5 ml (40 mmol) of methyl iodide are added with cooling in ice. After stirring at room temperature, the excess sodium hydride is carefully hydrolyzed while checking by means of thin layer chromatography. The reaction mixture is poured into water, the reaction product is subsequently extracted with methylene chloride and dried by means of sodium sulphate, and the solvent is distilled off in vacuo.

4.2 g (60.8% of theory) of 4-[(4,6-dimethyl-2-mercapto)-pyrimidyl]-methylthio-tert.-butyliminoanilide of melting point 136°–137° C. (recrystallization from ethyl acetate/n-hexane) are obtained.

The pyrimidyl-thio-carboxanilides of the formula (I) listed in the tables which follow are obtained in a corresponding fashion and according to the general information for the preparation:

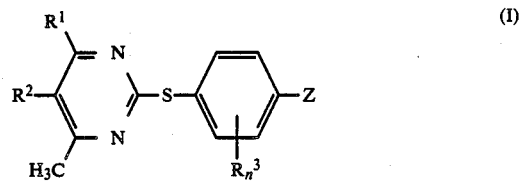

TABLE 3

$$Z = -N-C-C-R^6$$
with $R^4$, $R^5$, $R^7$, and $X$ substituents as shown.

| Example No. | $R^1$ | $R^2$ | $R^3$ | $R^4$ | $R^5$ | $R^6$ | $R^7$ | X | melting point °C. |
|---|---|---|---|---|---|---|---|---|---|
| 4 | CH$_3$ | H | H | CH$_3$ | CH$_3$ | CH$_3$ | CH$_3$ | O | 127–128 |
| 5 | CH$_3$ | H | H | —(CH$_2$)$_2$— | | H | H | O | 143–144 |
| 6 | CH$_3$ | H | H | —(CH$_2$)$_2$— | | CH$_3$ | CH$_3$ | O | 143 |
| 7 | CH$_3$ | H | H | —(CH$_2$)$_3$— | | H | H | O | 134–135 |
| 8 | CH$_3$ | H | H | —CH$_2$—CH=CH$_2$ | CH$_3$ | CH$_3$ | H | O | 97–98 |
| 9 | CH$_3$ | H | H | H | CH$_3$ | CH$_3$ | C$_2$H$_5$ | S | 117–118 |
| 10 | CH$_3$ | H | H | H | CH$_3$ | CH$_3$ | n-C$_3$H$_7$ | S | 109–111 |
| 11 | CH$_3$ | H | H | H | CH$_3$ | CH$_3$ | CH=CH$_2$ | S | 153–154 |
| 12 | CH$_3$ | H | H | H | CH$_3$ | —CCl$_2$—CH$_2$— | | S | 120–121 |
| 13 | CH$_3$ | H | H | H | CH$_3$ | —(CH$_2$)$_4$— | | S | 112–113 |
| 14 | CH$_3$ | H | H | H | CH$_3$ | CH$_3$ | H | S | 183–184 |
| 15 | CH$_3$ | H | H | H | C$_2$H$_5$ | C$_2$H$_5$ | H | S | 155–156 |
| 16 | CH$_3$ | H | H | H | CH$_3$ | CH$_3$ | —CH=CH$_2$ | S | 153–154 |
| 17 | CH$_3$ | H | H | —(CH$_2$)$_2$— | | H | H | S | 121–123 |
| 18 | CH$_3$ | H | H | —(CH$_2$)$_2$— | | CH$_3$ | CH$_3$ | S | |
| 19 | CH$_3$ | H | H | —(CH$_2$)$_3$— | | H | H | S | 169–170 |
| 20 | CH$_3$ | H | —3Cl | H | CH$_3$ | CH$_3$ | CH$_3$ | S | |
| 21 | CH$_3$ | H | —3CH$_3$ | H | CH$_3$ | CH$_3$ | CH$_3$ | S | 105 |
| 22 | CH$_3$ | H | —3OCH$_3$ | H | CH$_3$ | CH$_3$ | CH$_3$ | S | |
| 23 | CH$_3$ | CH$_3$ | H | H | CH$_3$ | CH$_3$ | CH$_3$ | S | |
| 24 | CH$_3$ | C$_2$H$_5$ | H | H | CH$_3$ | CH$_3$ | CH$_3$ | S | |
| 25 | H | H | H | H | CH$_3$ | CH$_3$ | CH$_3$ | S | 102 |
| 26 | CH$_3$ | H | H | H | CH$_3$ | CH$_3$ | i-C$_3$H$_7$ | S | 121 |
| 27 | CH$_3$ | H | 3-OCH$_3$ | —(CH$_2$)$_2$— | | CH$_3$ | CH$_3$ | O | 127 |
| 28 | H | CH$_3$ | H | —(CH$_2$)$_2$— | | CH$_3$ | CH$_3$ | O | 121 |
| 29 | H | H | 3-CH$_3$ | —(CH$_2$)$_2$— | | CH$_3$ | CH$_3$ | O | 106 |
| 30 | H | H | H | H | CH$_3$ | CH$_3$ | C$_2$H$_5$ | S | 76 |
| 31 | H | H | H | H | CH$_3$ | CH$_3$ | i-C$_3$H$_7$ | S | 100 |
| 32 | H | CH$_3$ | H | H | CH$_3$ | CH$_3$ | CH$_3$ | S | 120 |
| 33 | H | CH$_3$ | H | H | CH$_3$ | CH$_3$ | C$_2$H$_5$ | S | 70 |
| 34 | H | CH$_3$ | H | H | CH$_3$ | CH$_3$ | i-C$_3$H$_7$ | S | 88 |

TABLE 4

$$Z = -N=C-C-R^6$$
with $R^5$, $R^7$, and $R^8$–S substituents as shown.

| Example No. | $R^1$ | $R^2$ | $R^3$ | $R^5$ | $R^6$ | $R^7$ | $R^8$ | melting point °C. |
|---|---|---|---|---|---|---|---|---|
| 35 | CH$_3$ | H | H | CH$_3$ | CH$_3$ | CH$_3$ | C$_2$H$_5$ | 123–124 |
| 36 | CH$_3$ | H | H | CH$_3$ | CH$_3$ | CH$_3$ | i-C$_3$H$_7$ | 125–126 |
| 37 | CH$_3$ | H | H | CH$_3$ | CH$_3$ | CH$_3$ | CH$_2$—CH=CH$_2$ | 58–59 |
| 38 | CH$_3$ | H | H | CH$_3$ | CH$_3$ | CH$_3$ | CH$_2$—C≡CH | 94–95 |

TABLE 4-continued

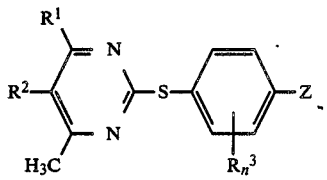

$$Z = -N=C-C-R^6$$
with $R^5$ above C, $R^8-S$ below left C, $R^7$ below right C

| Example No. | $R^1$ | $R^2$ | $R^3$ | $R^5$ | $R^6$ | $R^7$ | $R^8$ | melting point °C. |
|---|---|---|---|---|---|---|---|---|
| 39 | $CH_3$ | H | 3-Cl | $CH_3$ | $CH_3$ | $CH_3$ | $CH_3$ | |
| 40 | $CH_3$ | H | 3-$CH_3$ | $CH_3$ | $CH_3$ | $CH_3$ | $CH_3$ | |
| 41 | $CH_3$ | H | 3-$OCH_3$ | $CH_3$ | $CH_3$ | $CH_3$ | $CH_3$ | |
| 42 | $CH_3$ | $CH_3$ | H | $CH_3$ | $CH_3$ | $CH_3$ | $CH_3$ | |
| 43 | $CH_3$ | $C_2H_5$ | H | $CH_3$ | $CH_3$ | $CH_3$ | $CH_3$ | |
| 44 | H | H | H | $CH_3$ | $CH_3$ | $CH_3$ | $CH_3$ | 105 |
| 45 | H | Cl | H | $CH_3$ | $CH_3$ | $CH_3$ | $CH_3$ | |
| 46 | $CH_3$ | H | H | $CH_3$ | $CH_3$ | $i$-$C_3H_7$ | $CH_3$ | 65 |
| 47 | H | $CH_3$ | H | $CH_3$ | $CH_3$ | $CH_3$ | $CH_3$ | 100 |
| 48 | H | $CH_3$ | H | $CH_3$ | $CH_3$ | $CH_3$ | $C_2H_5$ | 53 |
| 49 | H | $CH_3$ | H | $CH_3$ | $CH_3$ | $CH_3$ | $-CH_2-CH=CH_2$ | 42 |
| 50 | H | $CH_3$ | 3-$CH_3$ | $CH_3$ | $CH_3$ | $CH_3$ | $CH_3$ | 76 |
| 51 | H | $CH_3$ | 3-$CH_3$ | $CH_3$ | $CH_3$ | $CH_3$ | $-CH_2-CH=CH_2$ | 01 |
| 52 | H | H | H | $CH_3$ | $CH_3$ | $CH_3$ | $-CH_2-CH=CH_2$ | 50 |
| 53 | H | H | H | $CH_3$ | $CH_3$ | $CH_3$ | $-CH_2-C\equiv CH$ | 116 |
| 54 | H | H | H | $CH_3$ | $CH_3$ | $C_2H_5$ | $-CH_2-CH=CH_2$ | 44 |
| 55 | H | H | H | $CH_3$ | $CH_3$ | $i$-$C_3H_7$ | $-CH_2-CH=CH_2$ | 60 |

Example A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the compounds according to preparation examples 2, 9, 10 and 13 show a very good herbicidal activity against weeds, such as, for example, chenopodium, helianthus, portulaca and sinapis, and a very good compatibility for useful plants, especially for barley and cotton.

It will be appreciated that the instant specification and claims are set forth by way of illustration and not limitation, and that various modifications and changes may be made without departing from the spirit and scope of the present invention.

What is claimed is:

1. (Thrice Amended) A pyrimidyl-thio carboxanilide of the formula

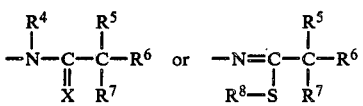

in which
$R^1$ represents hydrogen, a halogen, a $C_1$ to $C_6$ alkyl, a $C_1$ to $C_6$ alkoxy, a $C_1$ to $C_6$ alkylthio, trifluoromethyl or phenyl which is unsubstituted or substituted by a substituent selected from the group consisting of a halogen, methyl, ethyl, methoxy and trifluoromethyl,
$R^2$ represents hydrogen, a halogen, an alkyl having 1 to 6 carbons atoms or trifluoromethyl,
$R^3$ represents a halogen, methyl or methoxy,
n is 0, 1 or 2, and
z represents the group $$-N-C-C-R^6 \quad \text{or} \quad -N=C-C-R^6$$

(first with $R^4$, $R^5$ above, X, $R^7$ below; second with $R^5$ above, $R^8-S$, $R^7$ below)

where
X represents oxygen or sulfur,
$R^4$ represents hydrogen or hydroxyl,
a $C_1$ to $C_6$ alkyl, a $C_1$ to $C_6$ alkoxy,
a $C_3$ to $C_6$ alkenyl or a $C_3$ to $C_6$ alkynyl, with the proviso that $R^4$ does not represent hydrogen when X represents oxygen,
$R^5$ represents hydrogen, a halogen or an alkyl having 1 to 6 carbon atoms which is unsubstituted or mono- to nona-substituted by a halogen or
$R^4$ and $R^5$ together represents the group —$(CH_2)_2$— or —$(CH_2)_3$—,
$R^6$ and $R^7$ independently of one another, represent a halogen or an alkyl having 1 to 6 carbon atoms which is unsubstituted or mono- to nona-substituted, identically or differently by a halogen and
$R^8$ represents hydrogen, an alkyl having 1 to 6 carbon atoms, which is unsubstituted or singly to quintuply, identically or differently substituted by a substituent selected from the group consisting of a halogen, a $C_3$ to $C_8$ alkenyl and a $C_3$ to $C_6$ alkynyl.

2. A pyrimidyl-thio-carboxanilide of the formula (I) according to claim 1, in which $R^1$ represents hydrogen, fluorine, chlorine, bromine, straight-chain or branched $C_1$ to $C_4$ alkyl, straight-chain or branched $C_1$ to $C_4$ alkoxy or straight-chain or branched $C_1$ to $C_4$ alkylthio or trifluoromethyl, $R^2$ represents hydrogen, fluorine, chlorine, bromine, straight-chain or branched alkyl having 1 to 4 carbon atoms or trifluoromethyl, $R^3$ represents fluorine, chlorine, bromine, methyl or methoxy, n is 0, 1 or 2 and Z represents the group

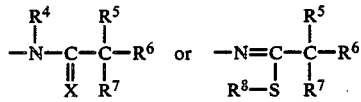

where

X represents oxygen or sulphur, $R^4$ represents hydrogen, hydroxyl, straight-chain or branched $C_1$ to $C_4$ alkyl, straight-chain or branched $C_1$ to $C_4$ alkoxy, straight-chain or branched $C_3$ to $C_4$ alkenyl or straight-chain or branched $C_3$ to $C_4$ alkynyl, with the proviso that $R^4$ does not represent hydrogen when X represents oxygen, $R^5$ represents hydrogen, fluorine, chlorine, bromine or straight-chain or branched alkyl having 1 to 4 carbon atoms which is unsubstituted or mono- to nona-substituted, identically or differently, by fluorine, chlorine or bromine, or $R^4$ and $R^5$ together represent the group $-(CH_2)_2-$ or $-(CH_2)_3-$, $R^6$ and $R^7$, independently of one another, represent fluorine, chlorine, bromine or straight-chain or branched alkyl having 1 to 4 carbon atoms which is unsubstituted or mono- to nona-substituted, identically or differently, by fluorine and chlorine and $R^8$ represents hydrogen, straight-chain or branched alkyl having 1 to 4 carbon atoms which is unsubstituted or singly to quintuply, identically or differently substituted by fluorine or chlorine, or straight-chain or branched $C_3$ to $C_6$ alkenyl or straight-chain or branched $C_3$ to $C_6$ alkynyl.

3. A pyrimidyl-thio-carboxanilide of the formula (I) according to claim 1, in which $R^1$ represents hydrogen, fluorine, chlorine, bromine, methyl, ethyl, methoxy, ethoxy, methylthio, ethylthio or trifluoromethyl, $R^2$ represents hydrogen, fluorine, chlorine, bromine, methyl, ethyl or trifluoromethyl, $R^3$ represents fluorine, chlorine, bromine, methyl or methoxy, n is 0, 1 or 2, Z represents the group

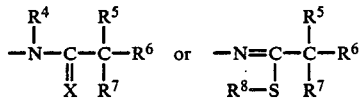

where

X represents oxygen or sulphur, $R^4$ represents hydrogen, hydroxyl, methyl, ethyl, methoxy, ethoxy, allyl or propargyl, with the proviso that $R^4$ does not represent hydrogen when X represents oxygen, $R^5$ represents hydrogen, fluorine, chlorine, bromine, methyl or ethyl, or $R^4$ and $R^5$ together represent the group $-(CH_2)_2-$ or $-(CH_2)_3-$, $R^6$ and $R^7$, independently of one another, represent fluorine, chlorine, bromine, methyl, ethyl, or iso-propyl and $R^8$ represents hydrogen, or $R^8$ represents methyl, ethyl, or iso-propyl which are unsubstituted or singly to quintuply, identically or differently substituted by fluorine, chlorine, allyl or propargyl.

4. A pyrimidyl-thio-carboxanilide according to claim 1, of the formula selected from the group consisting of

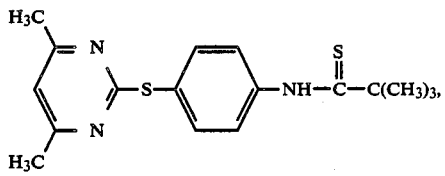

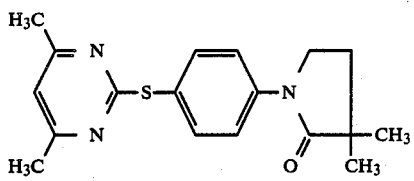

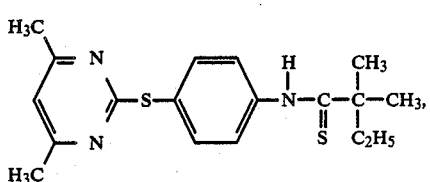

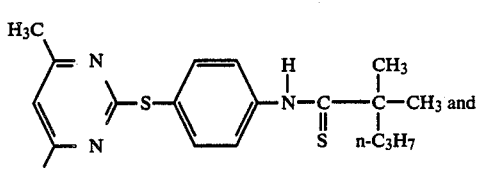

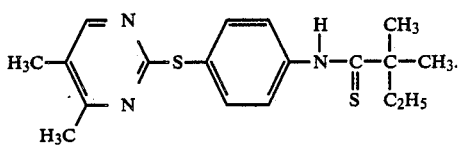

5. A herbicidal composition comprising a herbicidally effective amount of a pyrimidyl-thio-carboxanilide of the formula (I) according to claim 1 in admixture with a diluent.

6. A method for combating weeds, comprising applying to said weeds or to a locus from which it is desired to exclude such weeds a herbicidally effective amount of a pyrimidyl-thio-carboxanilide of the formula (I) according to claim 1.

7. A method according to claim 6, wherein the pyrimidyl-thio-carboxanilide is applied in an amount of 0.01 to 10 kg per hectare of soil surface.

8. A method according to claim 6, wherein the pyrimidyl-thio-carboxanilide is applied in an amount of 0.05 to 5 kg per hectare of soil surface.

* * * * *

UNITED STATES PATENT AND TRADEMARK OFFICE
CERTIFICATE OF CORRECTION

PATENT NO. : 4,765,824

DATED : August 23, 1988

INVENTOR(S) : Klaus Sasse, et al

It is certified that error appears in the above-identified patent and that said Letters Patent is hereby corrected as shown below:

| | |
|---|---|
| Title Page, under "Foreign Application Priority Data" | Delete "3344209" and substitute --3544209-- |
| Abstract, Col. 1, line 55, Col. 2, lines 51, 64, Col. 3, lines 47, 60, Col. 4, line 9, Col. 6, line 39, Col. 22, line 20, Col. 24, line 33 | Bottom of formula delete "$\mid R_n^3$" and substitute --$\mid R^3_n$-- |
| Col. 2, line 8 | After "oxygen" delete "and" and substitute --or-- |
| Col. 2, line 35 | Before "which" delete "in" |
| Col. 17, line 45 | Delete "presence" and substitute --process-- |
| Col. 20, lines 58-59 | Delete "mercaptopyrimidyl" and substitute --mercapto-pyrimidyl-- |
| Col. 22, Table 3, lines 2, 3 and 4 under "$R^4$" | Move "$-(CH_2)_2-$", "$-(CH_2)_2-$" and "$-(CH_2)_3-$" to lines 2, 3 and 4 in between columns "$R^4$" and "$R^5$" |
| Col. 22, Table 3, lines 14, 15, 16 under "$R^4$" | Move "$-(CH_2)_2-$", $-(CH_2)_2-$" and "$-(CH_2)_3-$" to lines 14, 15, 16 in between columns "$R^4$" and "$R^5$" |
| Col. 22, Table 3, lines 24, 25, 26 under "$R^4$" | Move "$-(CH_2)_2-$", "$-(CH_2)_2-$" and "$-(CH_2)_2-$" to lines 24, 25 and 26 in between "$R^4$" and "$R^5$" |

UNITED STATES PATENT AND TRADEMARK OFFICE
CERTIFICATE OF CORRECTION

PATENT NO. : 4,765,824

DATED : August 23, 1988

INVENTOR(S) : Klaus Sasse, et al

It is certified that error appears in the above-identified patent and that said Letters Patent is hereby corrected as shown below:

Col. 24, Example No. 51, last column     Delete "Ol" and substitute --Öl--

Signed and Sealed this

Fourth Day of April, 1989

Attest:

DONALD J. QUIGG

Attesting Officer     Commissioner of Patents and Trademarks